US012746383B2

(12) United States Patent
Feith et al.

(10) Patent No.: US 12,746,383 B2
(45) Date of Patent: Sep. 29, 2026

(54) NEEDLELESS CONNECTOR HAVING CHECK VALVE WITH CONCAVE FLOW SURFACE

(71) Applicant: CareFusion 303, Inc., San Diego, CA (US)

(72) Inventors: Raymond P. Feith, Chino Hills, CA (US); Randy Kipp, Upland, CA (US); Adel Shams, Fullerton, CA (US)

(73) Assignee: CAREFUSION 303, INC., San Diego, CA (US)

( * ) Notice: Subject to any disclaimer, the term of this patent is extended or adjusted under 35 U.S.C. 154(b) by 16 days.

(21) Appl. No.: 18/411,906

(22) Filed: Jan. 12, 2024

(65) Prior Publication Data

US 2024/0149043 A1 May 9, 2024

Related U.S. Application Data

(63) Continuation of application No. 16/745,220, filed on Jan. 16, 2020, now Pat. No. 11,904,131.

(51) Int. Cl.
*A61M 39/26* (2006.01)
*A61M 39/10* (2006.01)
(Continued)

(52) U.S. Cl.
CPC ............ *A61M 39/26* (2013.01); *A61M 39/10* (2013.01); *A61M 39/14* (2013.01); *A61J 1/1412* (2013.01);
(Continued)

(58) Field of Classification Search
CPC .......... A61M 39/26; A61M 2039/2433; A61M 39/10
See application file for complete search history.

(56) References Cited

U.S. PATENT DOCUMENTS 5,676,346 A 10/1997 Leinsing
5,782,816 A * 7/1998 Werschmidt .......... A61M 39/02 251/149.6

(Continued)

FOREIGN PATENT DOCUMENTS

CN 1666053 A 9/2005
CN 104136068 A 11/2014

(Continued)

OTHER PUBLICATIONS

Japanese Office Action for Application No. 2022-543526, dated Jan. 16, 2025, 4 pages including translation.

(Continued)

*Primary Examiner* — David Colon-Morales
(74) *Attorney, Agent, or Firm* — MASCHOFF BRENNAN

(57) ABSTRACT

A needleless connector may include a housing having an inlet port, an outlet port, and an inner surface defining an internal cavity extending between the inlet and outlet ports, and a compressible valve reciprocally disposed within the internal cavity. In a closed state, a top section of a head portion of the compressible valve may have a planar shape configured to contact and seal against the inner surface of the housing. In an open state, where the compressible valve is subject to an axial force, the top section of the head portion may be lodged between two pinch points between opposing walls of an inwardly angled portion of the internal surface. Additionally, in the open state, the top section of the head portion may have a non-planar shape defining a fluid path extending at least partially between opposing walls on an outwardly angled portion of the internal surface.

17 Claims, 7 Drawing Sheets

(51) Int. Cl.

| | |
|---|---|
| ***A61M 39/14*** | (2006.01) |
| *A61J 1/14* | (2023.01) |
| *A61J 1/20* | (2006.01) |
| *A61M 39/00* | (2006.01) |
| *A61M 39/24* | (2006.01) |

(52) U.S. Cl.
CPC ..... *A61J 1/2037* (2015.05); *A61M 2039/0009* (2013.01); *A61M 2039/2406* (2013.01); *A61M 2039/242* (2013.01); *A61M 2039/2433* (2013.01); *A61M 2039/2446* (2013.01)

(56) References Cited

U.S. PATENT DOCUMENTS

| | | | | |
|---|---|---|---|---|
| 6,123,320 A | | 9/2000 | Rasanow et al. | |
| 6,585,229 B2 | * | 7/2003 | Cote, Sr. | A61M 39/10 604/905 |
| 8,636,720 B2 | * | 1/2014 | Truitt | A61M 39/24 604/537 |
| 8,708,976 B1 | * | 4/2014 | Yeh | A61M 39/26 604/236 |
| 8,715,247 B2 | * | 5/2014 | Mansour | A61M 39/22 604/246 |
| 8,840,577 B1 | * | 9/2014 | Zollinger | A61M 39/22 604/167.03 |
| 9,067,049 B2 | * | 6/2015 | Panian | A61M 39/10 |
| 9,089,682 B2 | * | 7/2015 | Yeh | A61M 39/24 |
| 9,144,672 B2 | * | 9/2015 | Mansour | A61M 39/22 |
| 9,278,205 B2 | * | 3/2016 | Quach | A61M 39/10 |
| 9,370,651 B2 | * | 6/2016 | Zollinger | A61M 39/22 |
| 9,695,953 B2 | * | 7/2017 | Burnard | A61M 39/26 |
| 10,322,274 B2 | * | 6/2019 | Ueda | A61M 39/26 |
| 10,478,607 B2 | * | 11/2019 | Truitt | A61M 39/105 |
| 11,123,534 B2 | * | 9/2021 | Chen | A61M 39/10 |
| 11,904,131 B2 | * | 2/2024 | Feith | A61M 39/14 |
| 2005/0010177 A1 | * | 1/2005 | Tsai | A61M 39/26 604/256 |
| 2014/0276463 A1 | | 9/2014 | Mansour et al. | |
| 2014/0358073 A1 | * | 12/2014 | Panian | A61M 39/26 222/386.5 |
| 2016/0015961 A1 | | 1/2016 | Mansour et al. | |
| 2016/0178071 A1 | | 6/2016 | Javehari | |
| 2017/0072182 A1 | * | 3/2017 | Tsai | A61M 39/26 |
| 2017/0120028 A1 | * | 5/2017 | Burkholz | A61M 39/24 |

FOREIGN PATENT DOCUMENTS

| | | | | |
|---|---|---|---|---|
| CN | 110603069 A | | 12/2019 | |
| JP | 2009526566 A | | 7/2009 | |
| JP | 2015503990 A | | 2/2015 | |
| WO | WO-03018104 A2 | * | 3/2003 | A61M 39/26 |

OTHER PUBLICATIONS

International Search Report and Written Opinion for Application No. PCT/US2021/013133, dated Apr. 30, 2021, 14 pages.

Australian Office Action for Application No. 2021207591, dated Sep. 15, 2025, 3 pages.

Extended European Search Report for Application No. 25184126.8, dated Oct. 17, 2025, 10 pages.

Chinese Notification to Grant for Application No. 202180021590.4, dated Sep. 17, 2025, 9 pages including translation.

Chinese Office Action for Application No. 202180021590.4, dated May 31, 2025, 16 pages including translation.

Japanese Office Action for Application No. 2022-543526, dated Jul. 24, 2025, 4 pages including translation.

Mexican Office Action for Application No. MX/a/2022/008723, mailed Dec. 16, 2025, 11 pages including machine translation.

Canadian Office Action for Application No. 3,164,836, Jul. 6, 2026, 8 pages.

Mexican Office Action for Application No. MX/a/2022/008723, dated Jun. 8, 2026, 10 pages including translation of the requirements stated by the Examiner.

Indian Office Action for Application No. 202217045769, dated May 13, 2026, 6 pages.

* cited by examiner

NEEDLELESS CONNECTOR HAVING CHECK VALVE WITH CONCAVE FLOW SURFACE

CROSS REFERENCE TO RELATED APPLICATION

This application is a continuation of U.S. patent application Ser. No. 16/745,220, entitled "NEEDLELESS CONNECTOR HAVING CHECK VALVE WITH CONCAVE FLOW SURFACE," filed Jan. 16, 2020, the disclosure of which is incorporated herein by reference in its entirety.

TECHNICAL FIELD

The present disclosure relates generally to needleless connectors, and, in particular, to needleless connectors with a valve member defining a fluid path with a concave flow surface.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

Due to the nature of currently existing and/or prior art needleless valve geometries, fluid is commonly deposited on the face of the valve head upon removal of a medical implement (e.g., a mating male luer) used to apply an axial force to place the valve member in an open position. In these currently existing needleless valves, fluid deposited on the valve head will occasionally separate from the valve member and flow into the fluid path for administering to a patient, thereby causing anxiety along with potential blood stream diseases.

The description provided in the background section should not be assumed to be prior art merely because it is mentioned in or associated with the background section. The background section may include information that describes one or more aspects of the subject technology.

SUMMARY

An aspect of the present disclosure provides a needleless connector, comprising a housing and a compressible valve. The housing can have a proximal end defining an inlet port of the housing, a distal end including a base defining an outlet port of the housing, and an inner surface defining an internal cavity extending between the inlet and outlet ports. The compressible valve can be reciprocally disposed within the internal cavity of the housing and can be configured to contact at least a portion of the inner surface. The compressible valve can comprise a head portion and a compressible body portion extending distally from the head portion. In a closed state of the compressible valve, a top section of the head portion of the compressible valve can have a planar shape configured to contact and seal against the inner surface of the housing, and wherein in an open state, where the compressible valve is subject to an axial force, the top section of the head portion can be lodged between two pinch points thereof between opposing walls of an inwardly angled portion of the internal surface, and the top section of the head portion can have a non-planar shape defining a fluid path extending at least partially between opposing walls on an outwardly angled portion of the internal surface.

Some instances of the present disclosure provide a needleless connector, comprising a housing and a compressible valve. The housing can have a body including an inlet of the housing, a base including an outlet of the housing, and an internal cavity defined by an internal surface of the body. The compressible valve can be disposed within the internal cavity, and the compressible valve can comprise a head portion and a compressible body portion. The head portion can include a top section and a top surface. The top section can have an outer periphery configured to contact and seal against the internal surface in a closed state, and lodge between pinch points at opposing walls of the internal surface within the inlet when the head portion is subject to an axial force. The top surface can form an upper boundary of the top section, the top surface defining a fluid path which extends between the pinch points when the head portion is subject to the axial force. The compressible body portion can extend distally from the head portion.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 2A:
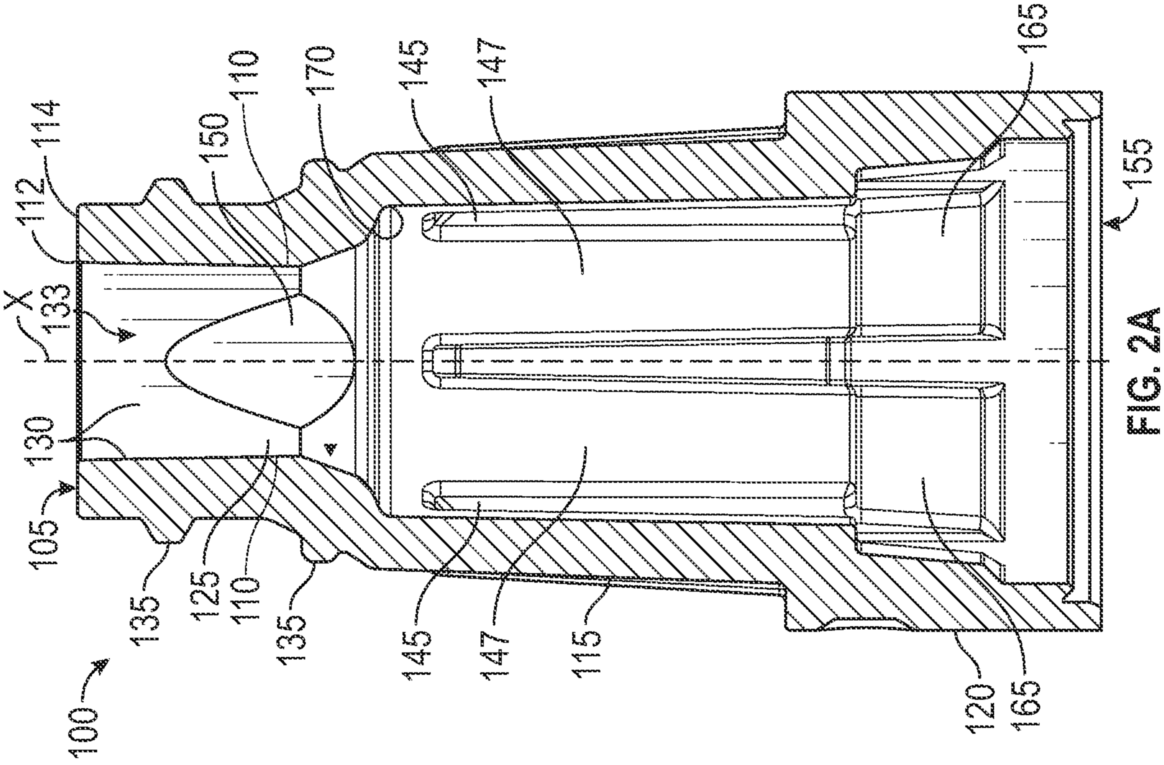
FIG. 2A is a cross-sectional view of the housing of the needleless connector of FIG. 1, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to a self-sealing, needleless connector that incorporates a flexible, compressible valve disposed within a housing of the connector, in which opening of the fluid path for administering of the medicinal fluid to the patient is not dependent on tilting or collapsing of the valve head. More particularly, various embodiments of the present disclosure are directed to a needleless connector having a housing and a compressible valve configured such that when subject to an axial force, tilting of the head portion of the compressible valve (which forms the fluid flow path in existing needleless connectors) is eliminated. Instead, in the various embodiments of the present disclosure, when subject to the axial force, a concave flow surface defining at least a portion of the fluid flow path is formed on a top surface of the head portion. As the axial force is removed, the top surface of the head portion (valve head) returns to the substantially flat or planar configuration, thereby creating a "face seal" before it is fully removed.

According to various embodiments of the present disclosure, when subjected to the axial force, the compressible valve is designed to allow two portions of an outer periphery of the top surface of the head portion (valve head) to be pinched or otherwise lodged between two points on opposing inwardly-angled internal walls of the housing. The two portions, and accordingly the two points on the housing (referred to herein as "pinch points") may be positioned about 180 degrees apart from each other. Accordingly, the housing inner diameter is designed to pinch the compressible valve at the two "pinch points," as well as to open up a flow path oriented 90 degrees to each of the pinch points without tilting or otherwise compressing the valve head. In particular, the housing may further be configured with a section of opposing outwardly-angled internal walls such that when the compressible valve is subject to the axial force and in the open state, a gap may be opened between the top section of the valve head and the outwardly-angled internal walls. The gap completes the fluid flow path by fluidly communicating the concave flow surface with the interior of the housing.

In order to prevent the valve head from tilting or otherwise compressing, the valve member of the various embodiments described herein may advantageously include a core member disposed axially along at least a portion of a length of the compressible valve. The core member may be disposed in the valve head extending along a central longitudinal axis of the needleless connector housing, and in some embodiments terminating at the compressible portion of the compressible valve. Accordingly, the core member may act as a support column to prevent the valve head from tilting or being otherwise deformed when the axial force is applied thereto.

When the two portions of the head portion are pinched between the two points on the opposing inwardly-angled inner walls of the housing, the top surface of the valve head transitions from a substantially flat planar surface to a concavely shaped recess or depression. The flow path may be defined by the concavely shaped recess or depression and the gap existing between the top section the valve head and the outwardly-angled internal walls. Accordingly, formation of the flow path occurs without tilting or compressing of the head portion (valve head) of the compressible valve.

As the medical implement (e.g., a mating male luer) is removed from the housing, the top surface of the valve head returns to the substantially flat or planar configuration, thereby creating a "face seal" before it is fully removed. The flat or planar shape of the top surface of the valve head advantageously minimizes the fluid capable of being deposited on the face, thereby preventing anxiety along with potential blood stream diseases commonly associated with fluids deposited on the face (top surface) of the valve head.

While the following description is directed to the administration of medical fluid to a patient by a medical practitioner using the disclosed needleless connector, it is to be understood that this description is only an example of usage and does not limit the scope of the claims.

Figure 1:
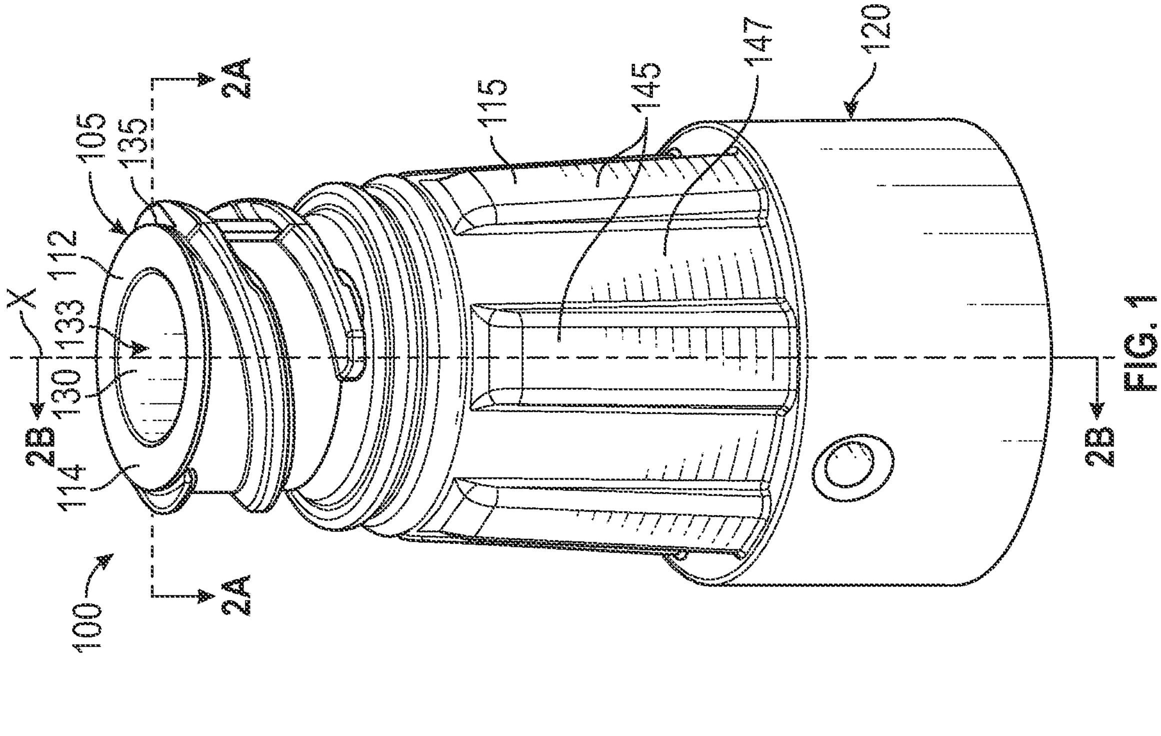
FIG. 1 is a perspective view of a housing of a needleless connector, in accordance with some embodiments of the present disclosure.

FIG. 1 is a perspective view of a housing 100 of a needleless connector, in accordance with some embodiments of the present disclosure. As depicted, the housing 100 may have a proximal end 105 defining an inlet port 112 of the housing 100 and a distal end 120 including a base 160 defining an outlet port 123 (illustrated in FIGS. 5A and 5B) of the housing 100, In some embodiments, the housing 100 may further include an inner surface 130 defining an internal cavity 133 which extends at least partially between the proximal and distal ends 105 and 120. The housing 100 may be formed of a body portion 115 and a base portion 160. However, in some embodiments, the housing may be formed from a combination of other pieces or parts similarly dimensioned to house the compressible valve 200 therein. In operation, a fluid pathway may be established through needleless connector from the inlet port 112 to the outlet port 123, for example.

Figure 2B:
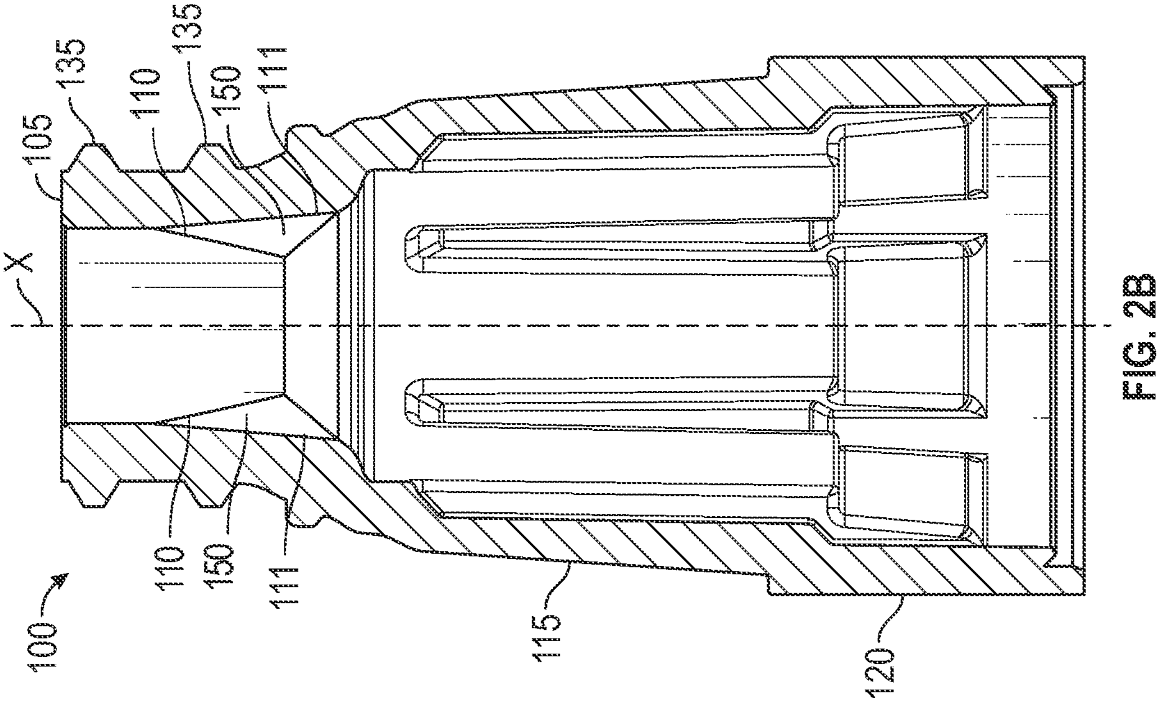
FIG. 2B illustrates the cross-sectional view of the housing of FIG. 2A rotated 90 degrees, in accordance with some embodiments of the present disclosure.

FIG. 2A is a cross-sectional view of the housing 100 of the needleless connector of FIG. 1, in accordance with some embodiments of the present disclosure. FIG. 2B illustrates the cross-sectional view of the housing of FIG. 2A rotated 90 degrees, in accordance with some embodiments of the present disclosure. As depicted, the housing 100 may include inlet port 112 for interfacing with a medical implement (e.g., a male luer 300 (illustrated in FIGS. 6A-6E)) and an opening 155 for connecting with the base 160 (shown in FIG. 5A) of the housing 100. As depicted, body portion 115 of the housing 100 may include one or more fluid flow channels 145 and one or more interior support columns 147. The lower section of the body portion 115 (e.g., a section proximal to the opening 155) may have an increased diameter and include one or more internal contact tabs 165. When assembled in a needleless connector, the one or more internal contact tabs 165 provide a radial force substantially orthogonal to the central longitudinal axis X onto a flange portion of a compressible valve (e.g., compressible valve 200 illustrated in FIGS. 3A-3C) that is arranged on a valve mount of the base portion 160.

In accordance with various embodiments of the present disclosure, the inlet port 112 may include a top port surface 114 and a channel defined in the internal cavity 133. The inlet port 112 may include engagement features 135 for coupling to another device (e.g., a fluid transfer assembly). For example, engagement features 135 may include cooperating mechanical elements, such as internal or external surface threads, detents, bayonet-type locking elements, etc., as well as other surface configurations, such as a tapered Luer surface for frictional engagement. In some embodiments, the inlet port 112 may define a female luer fitting with luer lock threading 135.

The inner surface 130 and the internal cavity 133 defined therein may extend longitudinally from the opening of the top port surface 114 of the inlet port 112 into the body portion 115 of the housing 100. In some embodiments, as depicted in FIG. 2A, the inner surface 130 may be formed of a first section of opposing walls 110 which are angled inwardly. In particular, the walls 110 may extend distally from the proximal end 105 of the housing 100 at an angle, which is slanted inwards towards the central longitudinal axis X of the housing 100. As referred to herein, proximally refers to an orientation toward the top port surface 114 of the housing 100, and distally refers to an orientation toward the base portion 160 or bottom of the housing 100, opposite the top port surface 114.

The opposing walls 110 may serve as inwardly angled portions of the internal surface 130 between which a top section 215 of the head portion 220 of the compressible valve 200 may become lodged when subject to the axial force F, as illustrated in, and as shall be further described with respect to FIGS. 6A-6C below.

In some embodiments, as depicted in FIG. 2B, the inner surface 130 may further be formed of a second section of opposing walls 111 which are angled outwardly. In particular, the walls 111 may extend distally from the proximal end 105 of the housing 100 at an angle, which is slanted outwards away from the central longitudinal axis X of the housing 100. The opposing walls 111 may serve as outwardly angled portions of the internal surface 130, whereby a gap may exist between the top section 215 of the head portion 220 of the compressible valve 200 and the internal surface 130 when the compressible valve 200 is subject to an axial force and in the open state, as illustrated in, and as shall be further described with respect to FIGS. 6D and 6E below. In this open state of the compressible valve, the gap serves as a flow path 150 through which fluid may flow into the cavity 130 within the body portion 115 of the housing, and out through the outlet 123, as shall be described further below.

In accordance with some embodiments, as depicted in FIG. 2B, the opposing walls 111 on the outwardly angled portion of the internal surface 130 may each be spaced approximately 90 degrees apart from the opposing walls 110 of the inwardly angled portion of the internal surface 130 on which pinch points P (illustrated in FIGS. 6A-6C) are located. As described herein the term "pinch point" refers to a position on the housing 100 where the compressible valve 200 becomes lodged otherwise "pinched" between the inwardly angled walls 110 of the housing 100 when the compressible valve 200 is subject to an axial force F which displaces the compressible valve 200 distally. The decreased clearance between the compressible valve 200 and the inwardly angled opposing walls 110 where the pinch points P are positioned resulting from the decrease in diameter of the internal cavity 130 at the inwardly angled walls 110, causes the top section 215 of the head portion 220 of compressible valve 200 to become lodged or otherwise "pinched" between angled opposing walls 110. The positions on the inwardly angled walls 110 between which the top section 215 of the head portion is "pinched" are referred to herein as the "pinch points." Continued application of the axial force to the top surface 205 of the head portion while the top section 215 is "pinched" between the opposing walls 110 causes the top surface 205 to contort, bend, or otherwise be reversibly or elastically deformed into the shape of a concave groove, depression, or recess 260 which forms a portion of the flow path 150 as shall be described in further detail with respect to FIGS. 6A-6E.

In some embodiments, an internal sealing edge 170 may be defined on the inner surface 130 of the housing 100. The internal sealing edge 170 may be a circumferential edge and configured for retaining the compressible valve 200 (illustrated in FIGS. 3A-3C) within the internal cavity 133 of the assembled needleless connector (illustrated in FIGS. 5A-5C). In operation, the internal sealing edge 170 may be arranged to provide blocking of fluid flow in conjunction with a primary seal portion of the compressible valve 200.

As depicted, fluid flow channels 145 may alternate with interior support columns 147. In some embodiments, fluid flow channels 145 may be smaller than the interior support columns 147. Additionally, fluid flow channels 145 may further extend into the lower portion of the body portion 115 between adjacent internal contact tabs 165. In this regard, a fluid path may be extended to the base portion 160 of the housing 100 coupled to the body portion 115 and further to the outlet port 123 (illustrated in FIGS. 5A and 5B).

Figure 3:
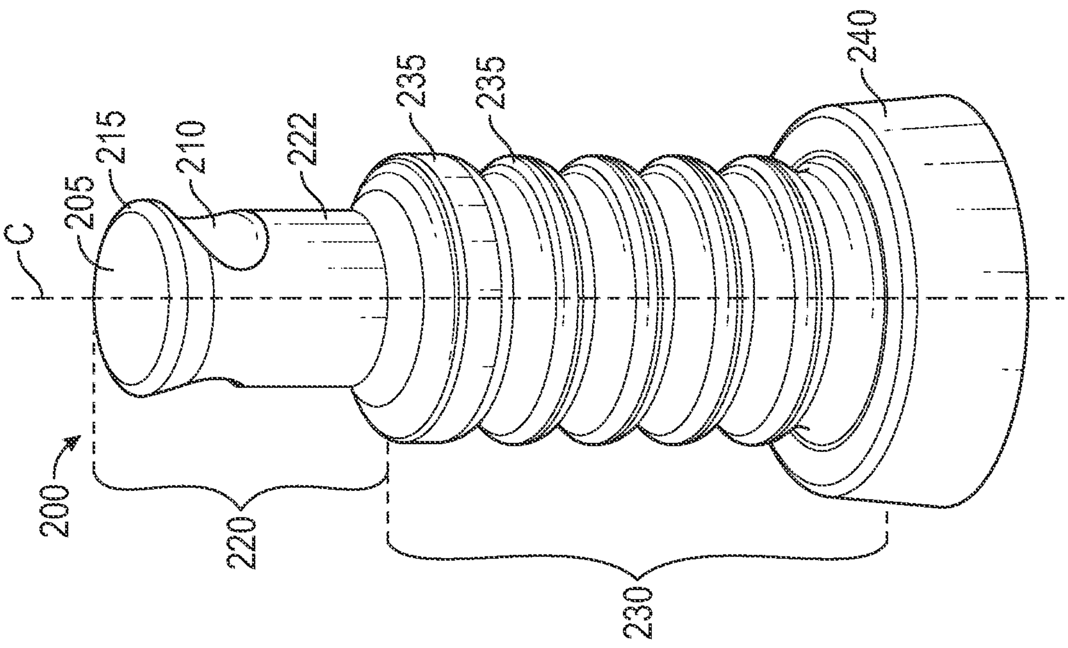
FIG. 3 is a perspective view illustrating an example of a compressible valve of a needleless connector, in accordance with some embodiments of the present disclosure.
Figure 4A:
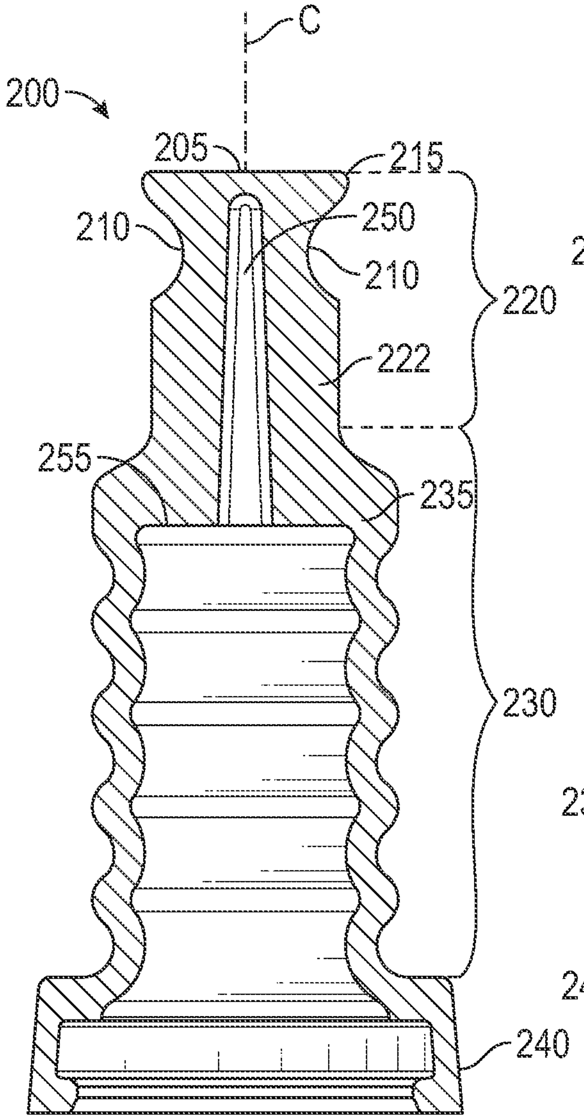
FIG. 4A is a cross-sectional view of the compressible valve of FIG. 3, in accordance with some embodiments of the present disclosure.
Figure 4B:
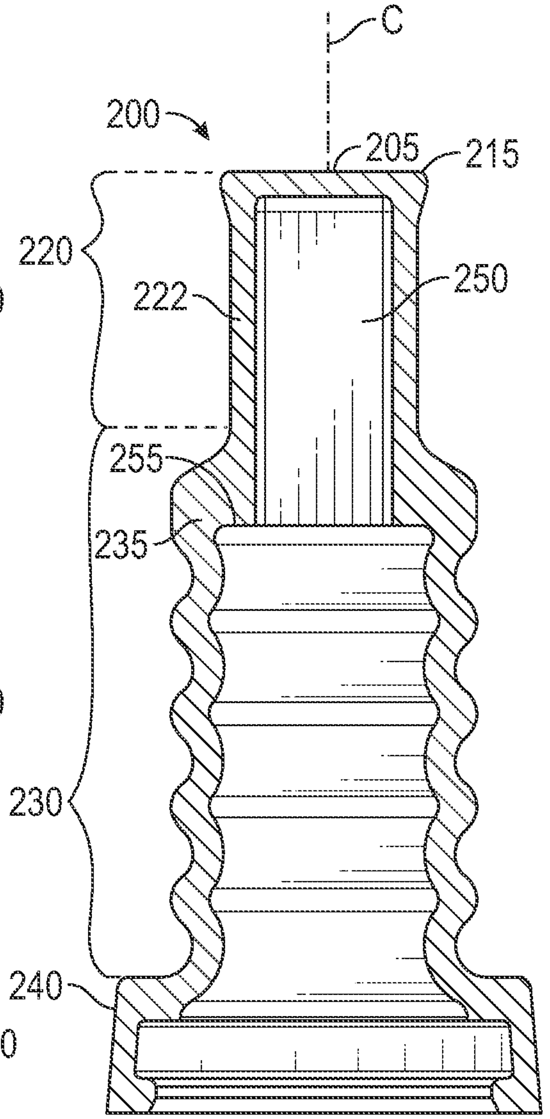
FIG. 4B illustrates the cross-sectional view of the compressible valve of FIG. 4A rotated 90 degrees, in accordance with some embodiments of the present disclosure.

FIG. 3 is a perspective view illustrating an example of a compressible valve of a needleless connector, in accordance with some embodiments of the present disclosure. FIG. 4A is a cross-sectional view of the compressible valve of FIG. 3, in accordance with some embodiments of the present disclosure. FIG. 4B illustrates the cross-sectional view of the compressible valve of FIG. 4A rotated 90 degrees, in accordance with some embodiments of the present disclosure.

FIGS. 3 to 4B illustrate in isolation an example compressible valve 200. Compressible valve 200 may include head portion 220, and compressible body portion 230 extending distally from the head portion 220. In certain embodiments, the head portion 220 includes a column section 222 having an axial center C substantially corresponding to the central longitudinal axis X of the needleless connector housing 100 when assembled therein. The central longitudinal axis C may extend longitudinally through the head portion 220 and the body portion 230 of the compressible valve 200. As depicted, the body portion 230 of the compressible valve 200 may have the same axial center as the head or other portions of the compressible valve 200. Moreover, the axial centers of compressible valve sections may be substantially aligned with the central longitudinal axis X of the needleless connector housing 100 in both a non-activated state (e.g., in isolation or within a connector but not displaced by a medical implement) and in an activated state (e.g., when an axial force is applied to the compressible valve 200 using the medical implement, for example male luer 300 (illustrated in FIG. 6A-6D)). Unlike existing compressible valves in which the axial centers of compressible valve sections will change and pivot in relation to the central longitudinal axis upon the compressible valve being activated by a medical implement, the compressible valve 200 of the various embodiments described herein is configured so as to maintain alignments of the axial center C of the compressible valve 200 with the central longitudinal axis X of the needleless connector housing 100. In particular, in order to achieve this configuration, the compressible valve 200 includes a core member 250 disposed axially along at least a portion of a length of the compressible valve 200. As depicted, the core member 250 is disposed in the head portion 220 extending along the central longitudinal axis X of the needleless connector housing 100 and terminating at the compressible portion 255 of the compressible valve 200. Accordingly, the core member 250 may act as a support column to prevent the head portion 220 of the compressible valve 200 from tilting or being otherwise deformed when the axial force is applied thereto.

Figure 5A:
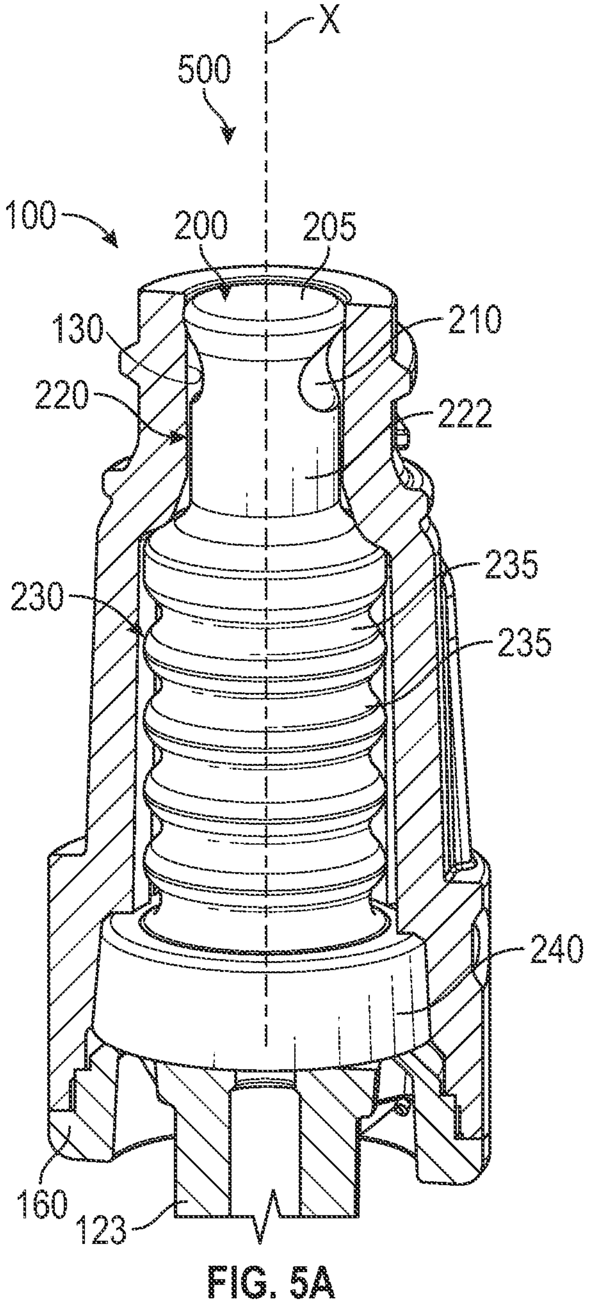
FIG. 5A is a perspective view of a partial cutaway of a housing of a needleless connector having a compressible valve installed therein in a closed position, in accordance with some embodiments of the present disclosure.
Figure 5B:
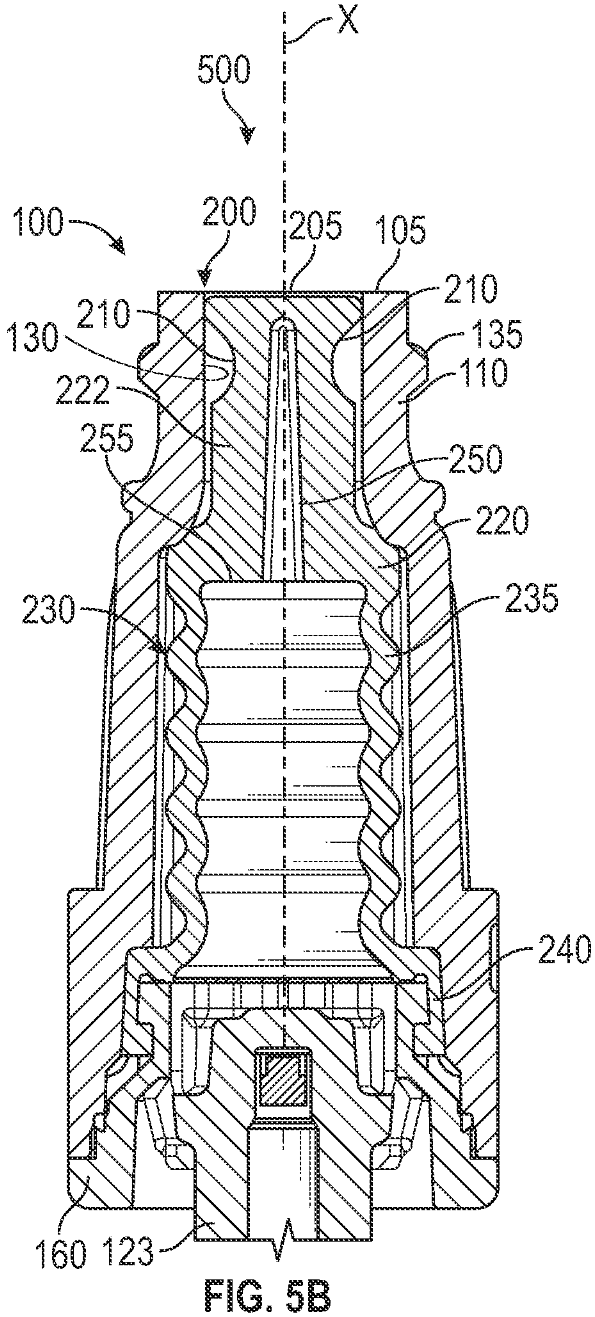
FIG. 5B is a cross-sectional view of the assembled needleless connector housing and compressible valve of FIG. 5A, in accordance with some embodiments of the present disclosure.

In accordance with some embodiments, the head portion 220 of the compressible valve 200 may have a top section 215 that includes a top surface 205. The top section 215 may be in the form of a circumferential lip or similar protrusion for slidably and sealably engaging with the inlet port 112 of the needleless connector housing 100. In the assembled configuration of the compressible valve 200 and the housing 100, the top surface 205 may be oriented at a perpendicular plane angle with respect to the central longitudinal axis X as illustrated in FIGS. 5A and 5B. In some embodiments, the head portion 200 includes at least one notch 210 disposed along the exterior thereof, adjacent to, and disposed distally to the top section 215. For example, as depicted, the head portion 220 may include two notches 210 disposed on opposing sides of the exterior of the column section 222 of body portion 220. The notches 210 may be configured as arcuate-shaped recesses within the column section 222. However, it is to be appreciated that the implementations of notches may comprise a variety of shapes and sizes, such as, but not limited to, notches having arcuate, triangular, polygonal, or various geometric cross-section shapes, for example. The aforementioned configuration of the notches 210 disposed on the head portion 200 allows for the top surface 205 of the compressible valve member 200 to bow distally when the head portion 220 is subjected to the axial force and the opposing ends of the top section 215 are pinched between and within the inner surface 133 of the housing 100. Accordingly, a concave flow channel may be formed or otherwise defined on the top surface 205 when the head portion 220 is subjected to the axial force, as shall be described in further detail with respect to FIGS. 6A-6D.

In some embodiments however, the column section 222 of head portion 220 of the compressible valve 200 may not include notch 210, but may instead have a discontinuity segment disposed thereon that operates in a similar manner as the notch 210. For example, one side or a portion of each side of the head portion 220 may be formed of a different material (or a same material with a different hardness value) than the remainder of the head portion 220.

According to various embodiments of the present disclosure, body portion 230 of the compressible valve 200 may be in the form of an elongated compressible cylindrical body including a series of concentrically disposed compressible segments 235. The concentrically disposed compressible segments 235 are configured such that when an axial force is applied to the head portion 220 of the compressible valve 200, the compressible segments 235 compress in order to allow for downward (i.e., distal) displacement of the compressible valve 200. Accordingly, a flow path fluidly connecting the inlet port 112 and the outlet port 123 may be opened, as shall be described in further detail with respect to FIGS. 6D and 6E. In some embodiments, the body portion 230 may further be coupled to or otherwise integrally formed with a flange portion 240 for securing the compressible valve 200 within the housing 100. As depicted, the flange portion 240 may be disposed along the compressible body portion 230 of the compressible valve.

The compressible valve 200 of the various embodiments described herein provides several advantages over prior art or otherwise existing compressible valves in which upon application of an axial force, the head portion further compresses, collapses, cants, and/or folds to open up a flow path in response to the axial force. Due to the compressed, collapsed, canted, and/or folded configurations of the prior art compressible valve head portions, it is not possible to maintain coaxial alignments of the axial center C of the compressible valve 200 with the central longitudinal axis X of the needleless connector housing 100. Accordingly, due to the geometrical configuration of the currently existing needleless valves, when the axial force is applied to the prior art compressible valves, deformation and compression of the head portion would prevent the desired pinching of the valve head portion between opposing walls to form the concave flow channel. Instead, the flow channel in the currently existing needleless valves would be formed as a result of the tilting, collapsing, and compressing of the compressible valves. Because the prior art compressible valve heads need additional time to decompress in order to return back to the undeformed state after removal of the axial force, the prior art compressible valves suffer the deficiency that during the time it takes to decompress, fluid collects and deposits on the top surface of the valve head. The depositing of fluid on the valve head is disadvantageous because the deposited fluid will occasionally separate from the valve and enter the fluid for administering the medicinal fluids to the patient, thereby causing anxiety along with possible blood stream disease.

In contrast, as the medical implement (e.g., male luer) applying the axial force F is removed from the housing 100 of the needleless connector of the various embodiments described herein, the top surface 205 of the valve head returns to the substantially flat or planar configuration before the medical implement is even fully removed, thereby advantageously creating a face seal before fluid deposits on the top surface 205. The flat or planar shape of the top surface of the valve head which creates the face seal advantageously minimizes the fluid capable of being deposited on the face. Accordingly, anxiety along with potential blood stream diseases commonly associated with fluids deposited on the face (top surface) of the valve head may be minimized or otherwise prevented from occurring.

Thus, the needleless connector 500 of the various embodiments described herein is configured such that when subject to an axial force F, tilting of the head portion 220 of the compressible valve 200 is eliminated. In particular, when subjected to the axial force F, the compressible valve 200 of the various embodiments described herein is designed to allow two portions of an outer periphery of the top surface 205 of the head portion (otherwise referred to as the valve head) 220 to be pinched or otherwise lodged between two pinch points on opposing inwardly-angled internal walls of the housing 100. Accordingly, the inner diameter of the housing 100 is designed to pinch the compressible valve at the two pinch points, and to also open up a flow path oriented 90 degrees to each of the pinch points without tilting or otherwise compressing the head portion 220. The housing 100 may further be configured with a section of opposing outwardly-angled internal walls such that when the compressible valve 200 is subject to the axial force and in the open state, a gap which forms part of the flow path 150 may be opened between the top section 215 of the head portion and the outwardly-angled internal walls 111.

Figure 5C:
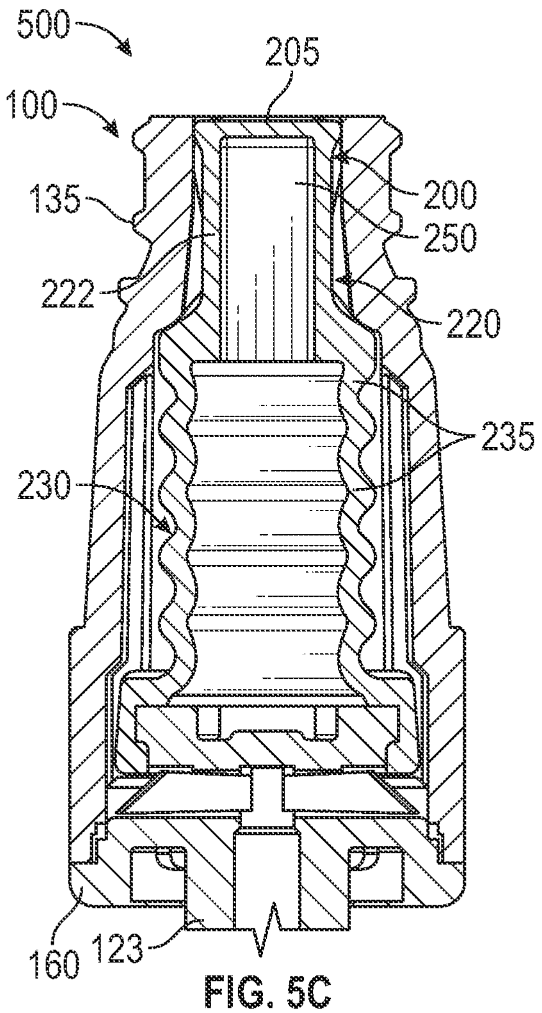
FIG. 5C is a cross-sectional view of the assembled needleless connector housing and compressible valve of FIG. 5B rotated 90 degrees, in accordance with some embodiments of the present disclosure.

FIG. 5A is a perspective view of a partial cutaway of a housing of a needleless connector 500 having a compressible valve 200 installed therein in a closed state, in accordance with some embodiments of the present disclosure. FIG. 5B is a cross-sectional view of the assembled needleless connector housing and compressible valve of FIG. 5A, in accordance with some embodiments of the present disclosure. FIG. 5C is a cross-sectional view of the assembled needleless connector housing and compressible valve of FIG. 5B rotated 90 degrees, in accordance with some embodiments of the present disclosure.

In accordance with various embodiments of the present disclosure, as previously described above, the distal end of the housing 100 forming the base 160 may include the outlet port 123 for interfacing with a medical implement, and a valve mount 175. The valve mount 175 may comprise a rim 180 that defines a recess with one or more air passages. The base 160 may further include the one or more fluid passages 145 for completing a fluid flow path from the internal cavity 133 of the housing 100 to the outlet port 123 of the base 160.

The base portion 160 may be dimensioned to be coupled to or otherwise integrally formed with the body portion 115 to create the housing 100 of the needleless connector 500. In some embodiments, the outlet port 123 may include engagement features for coupling to another device or coupling to interconnect tubing. For example, the outlet port 123 may comprise a male luer-taper fitting and luer lock threading (not shown) for medical device implement interconnection. However, engagement features of the outlet port 123 may include other cooperating mechanical elements.

FIGS. 5A-5C provide a longitudinal cross-sectional view of a needleless connector 500 showing the compressible valve 200 in the housing 100 formed by the body portion 115 and the base portion 160. The assembled needleless connector 500 as illustrated in FIGS. 5A-5C is in a sealed configuration such that any fluid from an interconnected fluid path coupled to the outlet port 123 is sealed from the inlet port 112. In some embodiments, the needleless connector 500 may be assembled such that the flange portion 240 of the compressible valve 200 is coupled, snapped, or otherwise attached onto the valve mount 175 of the base portion 160.

The internal cavity 133 of the housing 100 may be arranged on top of the compressible valve 200 coupled to the base portion 160 such that the head portion 220 of the compressible valve 200 is aligned and disposed within the inlet port 112. Upon assembly, the top surface 205 of the head portion 220 of the compressible valve 200 may have a resulting plane that is substantially perpendicular to the central longitudinal axis X or axial center of the column section 222 of the head portion 220 when the head portion 220 is engaged within the inlet port 112 of the housing 100. Additionally, the one or more internal contact tabs 165 (illustrated in FIG. 2A) disposed on the lower section of the body portion 115 surround and apply pressure to a sidewall of the flange portion 240 to secure and/or anchor the compressible valve 200 in the housing 100. In operation, the compressible valve 200 of the needleless connector can compress and collapse when an axial force is applied to the top surface 205 of the compressible valve 200 and expand and realign when the axial force is removed, as shall be described in further detail below.

Accordingly, the one or more internal contact tabs 165 may provide a radial force substantially orthogonal to the central longitudinal axis X onto the sidewall of the flange portion 240. In this regard, when the axial force is applied to the top surface 205 of the head portion 220 of the compressible valve 200, the effect of any resulting axial force through the compressible valve 200 onto the base 120 of the housing 100 is reduced if not eliminated. Such a resulting axial force applied onto the base 120 can work against or in derogation, for example, to a fused connection between the base 120 and the body portion 115, and over time may disadvantageously cause the fused connection to become breached and/or separated.

FIGS. 5A-5C depict the needleless connector 500 in a closed state, for example before an axial force F has been applied to the top surface 205 of the head portion 220 of the compressible valve 200, or in some embodiments, after the applied axial force F has been released from the top surface 205 of the head portion 220, and the top surface 205 has realigned with the opening of the inlet 112.

As depicted in FIGS. 5A and 5B, the inner surface 130 may be dimensioned so as to suitably house the compressible valve 200 therein. In particular, the inner surface 130 at the inlet 112 of the housing 100 may be dimensioned so as to slidably accommodate the top section 215 in the housing 100. In some embodiments, the top section 215 of the compressible valve member 200 may be configured to seal between the inner surface 130 of the housing and an outer periphery of the head portion 220 when the needleless connector 500 is in the closed state illustrated in FIGS. 5A-5C. In particular, in the closed state of the compressible valve 200, the top section 215 of the head portion 220 may have a planar or otherwise substantially flat shape configured to contact and seal against the inner surface 130 of the housing 100. Accordingly, fluid flow between the inlet port 112 and the outlet port 123 may be blocked.

Figure 6A:
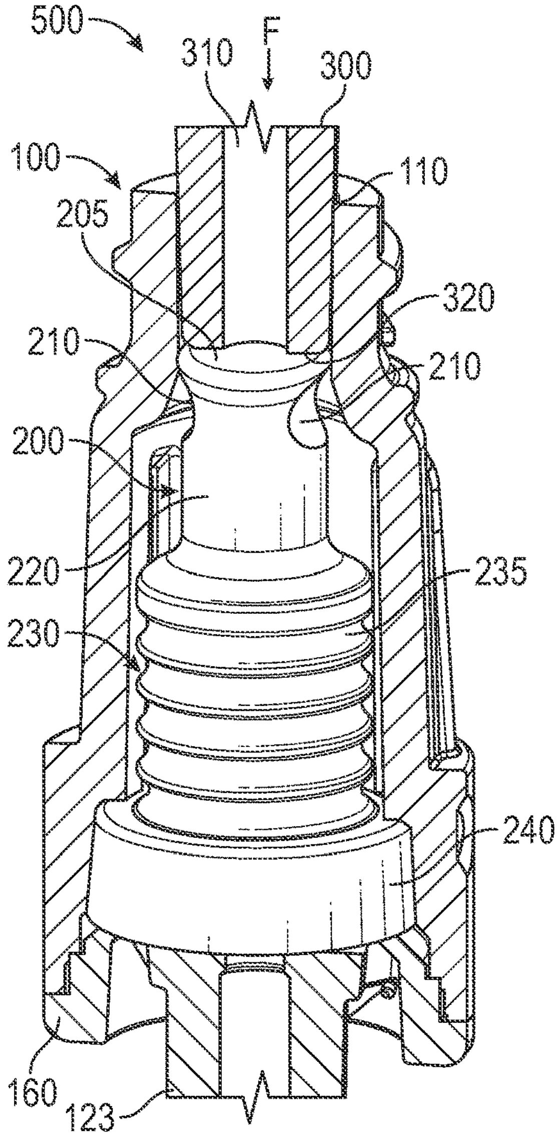
FIG. 6A is a perspective view of a partial cutaway of a housing of a needleless connector having a compressible valve installed therein with an axial force applied to place the valve in an open position, in accordance with some embodiments of the present disclosure.
Figure 6B:
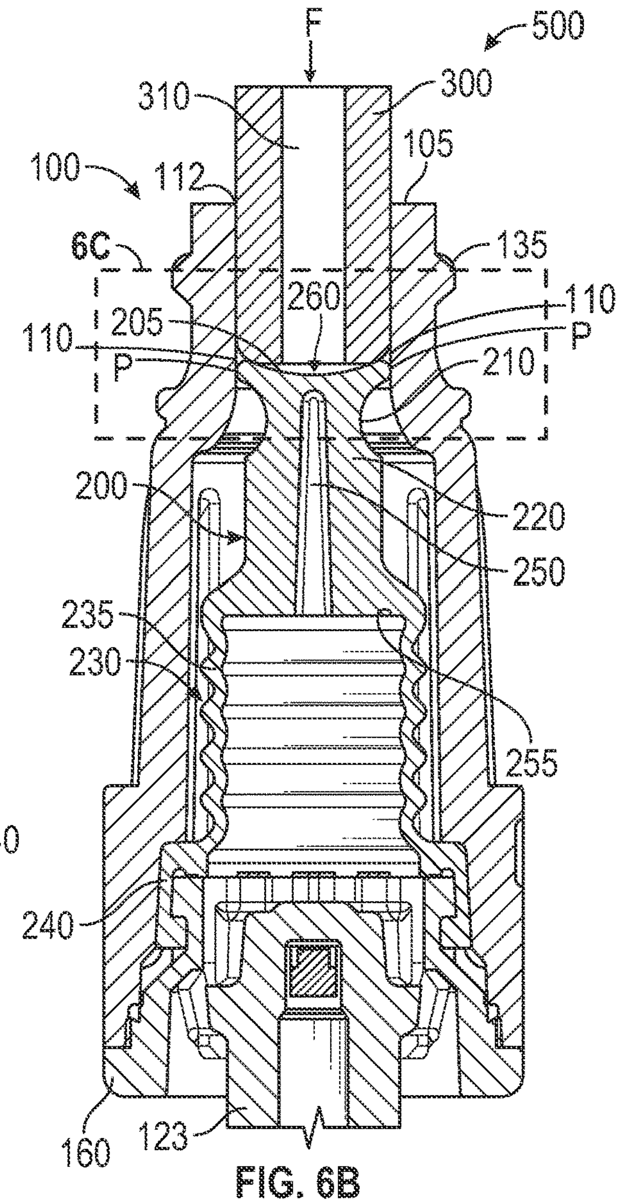
FIG. 6B is a cross-sectional view of the assembled needleless connector housing and compressible valve of FIG. 6A, in accordance with some embodiments of the present disclosure.
Figure 6C:
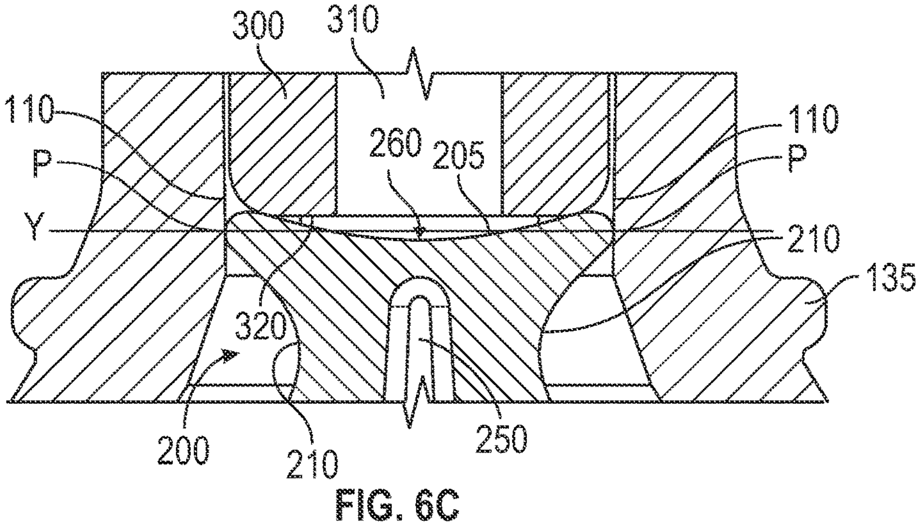
FIG. 6C is an enlarged partial view of a top surface of the compressible valve of FIG. 6B, in accordance with some embodiments of the present disclosure.

FIGS. 6A-6E depict the needleless connector 500 in an open state, for example when an axial force is been applied to the top surface 205 of the head portion 220 of the compressible valve. FIG. 6A is a perspective view of a partial cutaway of a housing 100 of a needleless connector 500 having the compressible valve 200 installed therein with an axial force applied to place the valve 200 in the open state, in accordance with some embodiments of the present disclosure. FIG. 6B is a cross-sectional view of the assembled needleless connector housing and compressible valve of FIG. 6A, in accordance with some embodiments of the present disclosure. FIG. 6C is an enlarged partial view of a top surface of the compressible valve of FIG. 6B, in accordance with some embodiments of the present disclosure.

FIGS. 6A-6C provide longitudinal cross-sectional views of the needleless connector 500 showing the compressible valve 200 upon initial entry of a medical implement 300 into the inlet port 112. As medical implement 300 (e.g., a male luer having a central channel 310, a syringe, or any other medical implement capable of transferring a fluid into the needleless connector 500) is inserted into the inlet port 112 of the needleless connector 500, an axial force F from the medical implement 300 is exerted onto the compressible valve 200 such that the compressible valve 200 is displaced distally within the housing 100. As the compressible valve 200 is displaced distally, an outer periphery of top section 215 of the head portion 220 may become lodged, at pinch points P, between the opposing walls 110 which extend distally from the proximal end 105 of the housing 100 at an angle which is slanted inwards towards the central longitudinal axis X of the housing 100. As the top section 215 becomes lodged between the pinch points P of the opposing walls 110 and the axial force continues to displace the compressible valve 200 distally, the top section 215 of the head portion 220 may slightly bow distally as illustrated at the top surface 205 in FIGS. 6B and 6C. As a result, the top surface 205 of the top section 215 of the compressible valve 200 may deform from the planar shape (where no axial force F was applied) to a non-planar shape 260. In accordance with some embodiments, the non-planar shape 260 may define at least a portion of the fluid path 150 extending at least partially between the opposing walls 111 on the outwardly angled portion of the internal surface 130, as shall be further described with respect to FIGS. 6D and 6E.

In particular, the non-planar shape 260 of the top section 215 that defines at least a portion of the flow path 150 may be in the shaped as a concave groove, depression, or recess 260 which opens into the flow path 150 as shall be described in further detail with respect to FIGS. 6A-6E. Accordingly, the flow path 150 may be defined by the concave groove, depression, or recess of the non-planar shape 260 and the gap existing between the top section 215 of the head portion 220 of the compressible valve 200 and the internal surface 130 in the open state of the compressible valve 200.

As depicted, during application of the axial force F, the core member 250 which is disposed axially along the length of the head portion 220 maintains axial alignment of a central longitudinal axis of the compressible valve member and a central longitudinal axis of the housing when the axial force is applied. In particular, the core member 250 may ensure that the head portion is not otherwise deformed or collapsed by the axial force F, other than the bowing or deflecting of the top surface 205 of the top section 215 where the concave recess 260 of the fluid flow path 150 is formed.

In some embodiments, the pinch points P may be spaced part from each other. In particular, as described above, each pinch point P may be located on opposite sides of the opposing walls 110, as depicted in FIGS. 6B and 6C. Accordingly, in some embodiments, the pinch points P may be positioned on the opposing walls 110 at an angle approximately 180 degrees apart from each other. For example, as depicted in FIG. 6C, the pinch points P may be positioned opposite and across from each other along a common axis Y extending through the pinch points P.

Figure 6D:
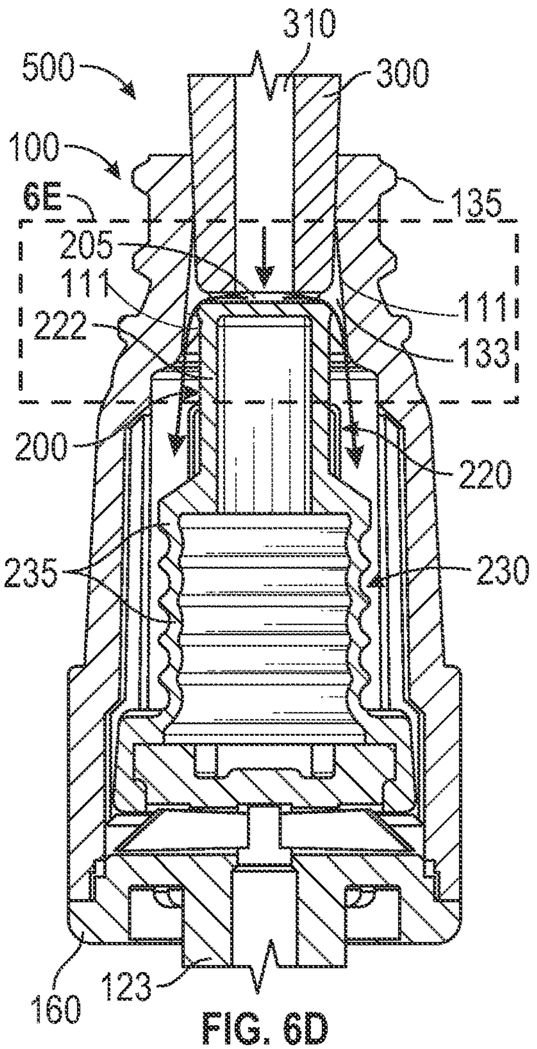
FIG. 6D is a cross-sectional view of the assembled needleless connector housing and compressible valve of FIG. 6B rotated 90 degrees, in accordance with some embodiments of the present disclosure.
Figure 6E:
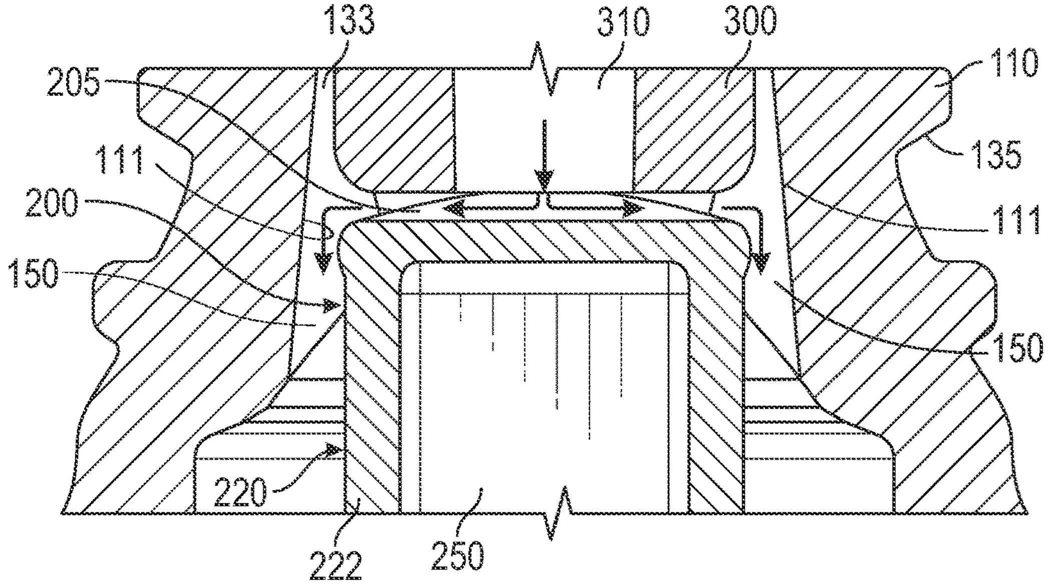
FIG. 6E is an enlarged partial view of a top surface of the compressible valve of FIG. 6D, in accordance with some embodiments of the present disclosure.

FIG. 6D is a cross-sectional view of the assembled needleless connector housing 100 and compressible valve 200 of FIG. 6B rotated 90 degrees, in accordance with some embodiments of the present disclosure. FIG. 6E is an enlarged partial view of the top surface 205 of the compressible valve 200 of FIG. 6D, in accordance with some embodiments of the present disclosure. FIGS. 6D and 6E depict provide longitudinal cross-sectional views of the needleless connector 500 showing the compressible valve 200 upon initial entry of a medical implement 300 into the inlet port 112.

As previously described with respect to FIGS. 6A-6C, the recess defined by the non-planar shape 260 formed on the top surface 205 of the head portion 220 as a result of application of the axial force F in conjunction with pinching of the top section 215 between pinch points P of opposing walls 110 of the housing may define a portion of fluid path 150 extending at least partially between opposing walls 111 on the outwardly angled portion of the internal surface 130. FIGS. 6D and 6E provide longitudinal cross-sectional views of the needleless connector 500 rotated 90 degrees from the views illustrated in FIGS. 6A-6C. As previously described, the medical implement 300 may be used to apply the axial force F to distally displace the compressible valve 200 within the housing 100. As the compressible valve 200 is displaced distally and the outer periphery of top section 215 of the head portion 220 becomes lodged at pinch points P on opposing inwardly-angled walls 110, the fluid path (illustrated by the arrows) defined at least in part by the non-planar shape of the top section 205 of the head portion between the pinch points P is opened into the internal cavity 133 of the housing 100. As previously discussed, the opposing walls 111 may serve as outwardly angled portions of the internal surface 130 where a gap may exist between the top section 215 of the head portion 220 of the compressible valve 200 and the internal surface 130 when the compressible valve 200 is subject to an axial force and in the open state. In this open state of the compressible valve, the gap serves as a path through which fluid may flow into the cavity 130 within the body portion 115 of the housing, and out through the outlet 123. In accordance with some embodiments, as previously described with respect to FIG. 2B, the opposing walls 111 on the outwardly angled portion of the internal surface 130 may each be spaced approximately 90 degrees apart from the opposing walls 110 of the inwardly angled portion of the internal surface 130 on which pinch points P (illustrated in FIGS. 6A-6C) are located. Accordingly, the flow path 150 defined by the concave groove, depression, or recess 260 and the gap existing between the top section 215 of the head portion 220 of the compressible valve 200 and the internal surface 130 in the open state of the compressible valve 200, may be oriented orthogonally to the common axis Y extending through the pinch points P.

As depicted, in the open state of the compressible valve 200, fluid may flow from the central channel 310 of the medical implement 300 positioned in the inlet 112 into the concave shaped recess 260 of flow path 150 in the cavity 133, and out through the outlet port 123. A medical fluid may thus be administered to a patient through the outlet port 123 of the housing 100.

In some embodiments, once the axial force F is removed and the compressible valve 200 transitions back to the closed state, pinching force between the inner surface 130 of the housing 100 and the top section 215 of the head portion 220 at each of the pinch points may be released and the top section 215 where the concave shaped recess 260 of fluid path 150 is defined may transition from the concave shape back to the planar shape.

Accordingly, the configuration of the needleless connector 500 of the various embodiments described herein is advantageously designed to pinch the compressible valve 200 at the two "pinch points," of the housing 100 in order to open up a flow path oriented 90 degrees to each of the pinch points without tilting or otherwise compressing the valve head. In order to prevent the valve head from tilting or otherwise compressing, the core member 250 is disposed axially along at least a portion of a length of the compressible valve, extending along a central longitudinal axis of the needleless connector housing, and in some embodiments terminating at the compressible portion of the compressible valve. Advantageously, the core member may act as a support column to prevent the valve head from tilting or being otherwise compressed or deformed when subject to the axial force F. As previously described, when the two portions of the head portion 220 are pinched between the two pinch points P, the top surface 205 of the valve head transitions from a substantially flat planar surface to a concavely shaped recess or depression. The flow path may thus be defined by the concavely shaped recess or depression and the gap existing between the top section the valve head and the outwardly-angled internal walls. Accordingly, contrary to some compressible valves, formation of the flow path does not occur as a result of tilting or compressing of the head portion (valve head) of the compressible valve, but instead due to the pinching and formation of the concave recess on the top surface 205.

As the medical implement 300 applying the axial force F is removed from the housing 100, the top surface 205 of the valve head may return to the substantially flat or planar configuration, thereby advantageously creating a face seal before even it is fully removed from the housing 100. The flat or planar shape of the top surface 205 of the head portion 220 which creates the face seal advantageously minimizes the fluid capable of being deposited on the top surface 205 (i.e., the valve face). Accordingly, anxiety along with potential blood stream diseases commonly associated with fluids deposited on the face (top surface) of the valve head may be minimized or otherwise prevented from occurring.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A needleless connector, comprising: a housing having a proximal end defining an inlet port of the housing, a distal end including a base defining an outlet port of the housing, and an inner surface defining an internal cavity extending between the inlet and outlet ports; and a compressible valve reciprocally disposed within the internal cavity and configured to contact at least a portion of the inner surface, the compressible valve comprising a head portion and a compressible body portion extending distally from the head portion, wherein: in a closed state of the compressible valve, a top section of the head portion of the compressible valve has a planar shape configured to contact and seal against the inner surface of the housing; and in an open state, where the compressible valve is subject to an axial force: the top section of the head portion is lodged between two pinch points thereof between opposing walls of an inwardly angled portion of the internal surface; and the top section of the head portion has a non-planar shape defining a fluid path extending at least partially between opposing walls on an outwardly angled portion of the internal surface.

Clause 2. The needleless connector of Clause 1, wherein the two pinch points are spaced approximately 180 degrees apart from each other.

Clause 3. The needleless connector of Clause 2, wherein the opposing walls on the outwardly angled portion of the internal surface are each spaced approximately 90 degrees apart from the opposing walls of the inwardly angled portion of the internal surface.

Clause 4. The needleless connector of Clause 2, wherein the fluid path is oriented orthogonally to a common axis extending through the pinch points.

Clause 5. The needleless connector of Clause 2, wherein the non-planar shape of the top section of the head portion defining the fluid path comprises a concave shape.

Clause 6. The needleless connector of Clause 5, wherein when the axial force is removed, pinching force between the inner surface of the housing and the head portion at each of the pinch points is released and the top section where the fluid path is defined transitions from the concave shape back to the planar shape.

Clause 7. The needleless connector of Clause 6, wherein the planar shaped top surface of the head portion creates a face seal between the head portion and the inner surface of the housing.

Clause 8. The needleless connector of any of Clauses 1 to 7, wherein the compressible valve further comprises a core member disposed axially along at least a portion of a length of the compressible valve, the core member configured to maintain axial alignment of a central longitudinal axis of the compressible valve and a central longitudinal axis of the housing when the axial force is applied.

Clause 9. The needleless connector of any of Clauses 1 to 8, wherein the head portion comprises at least one notch disposed along an exterior of the head portion.

Clause 10. The needleless connector of any of Clauses 1 to 9, wherein the compressible valve further comprises a flange portion disposed along the body portion for securing the compressible valve within the housing.

Clause 11. A needleless connector, comprising: a housing having a body including an inlet of the housing, a base including an outlet of the housing, and an internal cavity defined by an internal surface of the body; and a compressible valve disposed within the internal cavity, the compressible valve comprising; a head portion including: a top section having an outer periphery configured to (i) contact and seal against the internal surface in a closed state, and (ii) lodge between pinch points at opposing walls of the internal surface within the inlet when the head portion is subject to an axial force; and a top surface forming an upper boundary of the top section, the top surface defining a fluid path which extends between the pinch points when the head portion is subject to the axial force; and a compressible body portion extending distally from the head portion.

Clause 12. The needleless connector of Clause 11, wherein the pinch points are spaced approximately 180 degrees apart from each other.

Clause 13. The needleless connector of any of Clauses 11 or 12, wherein the opposing walls of the internal surface on which the pinch points are located are angled inwardly towards each other.

Clause 14. The needleless connector of any of Clauses 1 to 13, wherein the top surface of the head portion has a planar shape configured to contact and seal against the inner surface of the housing when the head portion is not subject to the axial force.

Clause 15. The needleless connector of any of Clauses 1 to 14, wherein the fluid path is defined between opposing walls of the internal surface which are angled outwardly away from each other.

Clause 16. The needleless connector of Clause 15, wherein the outwardly angled opposing walls on the internal surface are each spaced approximately 90 degrees apart from the pinch points.

Clause 17. The needleless connector of Clause 15, wherein the top surface of the head portion defining the fluid path has a non-planar shape when the compressible valve subject to the axial force is in an open state.

Clause 18. The needleless connector of Clause 17, wherein the non-planar shape of the top section of the head portion defining the fluid path comprises a concave shape.

Clause 19. The needleless connector of Clause 18, wherein when the axial force is removed, pinching force between the inner surface of the housing and the head portion at each of the pinch points is released and the top surface where the fluid path is defined transitions from the concave shape to a planar shape.

Clause 20. The needleless connector of any of Clauses 1 to 18, wherein the fluid path is oriented orthogonally to a common axis extending through the pinch points.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector, comprising:

a housing having an upper portion comprising an inlet port, a lower portion comprising an opening, and an inner surface forming an inner cavity extending from the inlet port in a distal direction to the opening, the upper portion having a first section of opposing walls that extend distally at an angle radially inward, relative to a longitudinal axis of the housing, and a second section of opposing walls that are axially aligned with the first section of opposing walls and extend distally at an angle radially outward, relative to the longitudinal axis of the housing; and a compressible valve having a head portion and a compressible body portion extending distally from the head portion, the compressible valve positioned within the inner cavity and compressible between a closed state and an open state, wherein, in the closed state, a top section of the head portion is engaged against the inner surface to resist movement of a fluid between the inlet port and the inner cavity and comprises a top surface, and in the open state, the top section of the head portion is engaged against the first section of opposing walls that are angled radially inward such that the top section is pinched between two points on the first section of opposing walls to bias the top section of the head portion such that the top surface forms a concave shape and a fluid flow path is formed between the top section of the head portion and the inner surface.

2. The needleless connector of claim 1, wherein the first section of opposing walls are spaced approximately 180 degrees apart from each other.

3. The needleless connector of claim 1, wherein the head portion comprises at least one notch disposed along an outer surface of the head portion.

4. The needleless connector of claim 1, wherein an inner surface of the head portion forms a core cavity extending in a direction from the compressible body portion toward the top section of the head portion.

5. The needleless connector of claim 4, wherein an inner surface of the compressible body portion forms a void extending from the opening to the core cavity.

6. The needleless connector of claim 1, wherein, in the open state, the fluid flow path is formed by a gap between the top section of the head portion and the second section of opposing walls.

7. The needleless connector of claim 1, wherein the first section of opposing walls and the second section of opposing walls are axially aligned.

8. The needleless connector of claim 1, wherein the second section of opposing walls are radially oriented 90 degrees from the first section of opposing walls.

9. A needleless connector, comprising:

a housing having an upper portion comprising an inlet port, a lower portion comprising an opening, and an inner surface forming an inner cavity extending from the inlet port in a distal direction to the opening, the inner cavity along the upper portion having a diameter that decreases along a first section of opposing walls in the distal direction away from the inlet port, wherein the diameter decreases relative to a second section of opposing walls that are axially aligned with the first section of opposing walls, and the second section of opposing walls comprise a width that increases in the distal direction away from the inlet port; and a compressible valve having a head portion and a compressible body portion extending distally from the head portion, the compressible valve positioned within the inner cavity and compressible between a closed state and an open state, wherein, in the closed state, a top section of the head portion is engaged against the inner surface to resist movement of a fluid between the inlet port and the inner cavity and comprises a top surface, and in the open state, the top section of the head portion is engaged against the first section of opposing walls to bias the top section of the head portion such that the top surface forms a concave shape and a fluid flow path is formed between the top section of the head portion and the second section of opposing walls.

10. The needleless connector of claim 9, wherein the first section of opposing walls are spaced approximately 180 degrees apart from each other.

11. The needleless connector of claim 9, wherein the head portion comprises at least one notch disposed along an outer surface of the head portion.

12. The needleless connector of claim 9, wherein an inner surface of the head portion forms a core cavity extending in a direction from the compressible body portion toward the top section of the head portion.

13. The needleless connector of claim 12, wherein an inner surface of the compressible body portion forms a void extending from the opening to the core cavity.

14. The needleless connector of claim 9, wherein, in the open state, the fluid flow path is formed by a gap between the top section of the head portion and the second section of opposing walls.

15. The needleless connector of claim 9, wherein the second section of opposing walls are radially oriented 90 degrees from the first section of opposing walls.

16. A needleless connector, comprising:

a housing having a first port, a base having a second port, and an inner surface forming an inner cavity extending from the first port in a distal direction to the second port, the inner cavity having a first section of opposing walls having a width that decreases in the distal direction away from the first port, wherein the width decreases relative to a second section of opposing walls axially aligned with the first section of opposing walls, and the second section of opposing walls comprise a width that increases in the distal direction away from the first port; and a compressible valve having a head portion and a compressible body portion extending distally from the head portion, the compressible valve positioned within the inner cavity and compressible between a closed state and an open state, wherein, in the closed state, a top section of the head portion is engaged against the inner surface to resist movement of a fluid between the first port and the inner cavity, and in the open state, the top section of the head portion is engaged against the first section of opposing walls to bias the top section of the head portion such that a top surface of the top section forms a concave shape and a fluid flow path is formed between the top section of the head portion and the second section of opposing walls.

17. The needleless connector of claim 16, wherein the second section of opposing walls are radially oriented 90 degrees from the first section of opposing walls.

* * * * *